United States Patent
Iuel (10) Patent No.: US 9,968,241 B2
(45) Date of Patent: May 15, 2018

(54) APPARATUS FOR MAINTAINING A TENSIONED PULL-WIRE IN AN ENDOSCOPE

(71) Applicant: Ambu A/S, Ballerup (DK)

(72) Inventor: Hans Henrik Iuel, Sorø (DK)

(73) Assignee: AMBU A/S, Ballerup (DK)

( * ) Notice: Subject to any disclaimer, the term of this patent is extended or adjusted under 35 U.S.C. 154(b) by 0 days. days.

(21) Appl. No.: 14/766,959

(22) PCT Filed: Feb. 22, 2013

(86) PCT No.: PCT/DK2013/050049
§ 371 (c)(1),
(2) Date: Aug. 10, 2015

(87) PCT Pub. No.: WO2014/127780
PCT Pub. Date: Aug. 28, 2014

(65) Prior Publication Data
US 2015/0366436 A1     Dec. 24, 2015

(51) Int. Cl.
*A61B 1/005* (2006.01)
*A61B 1/00* (2006.01)
(Continued)

(52) U.S. Cl.
CPC ............ *A61B 1/0057* (2013.01); *A61B 1/005* (2013.01); *A61B 1/008* (2013.01); *A61B 1/0051* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS

| 609,750 A | 8/1898 | Bowden |
|---|---|---|
| 4,203,430 A | 5/1980 | Takahasi |

(Continued)

FOREIGN PATENT DOCUMENTS

| CN | 1692872 | 11/2005 |
|---|---|---|
| CN | 102271571 | 12/2011 |

(Continued)

OTHER PUBLICATIONS

First Examination Report in corresponding Chinese patent application No. 201380073505.4, dated Jun. 20, 2016, and translation thereof, 12 pgs.

(Continued)

*Primary Examiner* — Ryan Henderson
(74) *Attorney, Agent, or Firm* — Faegre Baker Daniels LLP (57) ABSTRACT

A control mechanism for an endoscope (1) comprising a Bowden cable. the Bowden cable has an outer guide tube (9) having a first length between a proximal end and a distal end of said outer guide tube (9) and an inner pull-wire (15) having a second length between a proximal end and a distal end of said inner pull-wire (15). The second length is longer than the first length. The outer guide tube (9) comprises a first guide tube section (9') and a second guide tube section, where said first guide tube section (9') has plastic and elastic properties, which are different from the plastic and elastic properties of said second guide tube section (9").

2 Claims, 5 Drawing Sheets

(51) Int. Cl.
*A61B 17/00* (2006.01)
*A61M 25/01* (2006.01)
*A61B 1/008* (2006.01)

(52) U.S. Cl.
CPC ........ *A61B 1/0052* (2013.01); *A61B 1/00066* (2013.01); *A61M 25/0133* (2013.01); *A61M 25/0147* (2013.01); *A61B 1/00103* (2013.01); *A61B 2017/003* (2013.01); *A61B 2017/00318* (2013.01); *A61B 2017/00323* (2013.01)

(58) Field of Classification Search
CPC ... A61B 1/0056; A61B 1/0057; A61B 1/0058; A61B 1/008; A61B 1/01; A61B 2017/003; A61B 2017/00305; A61B 2017/00309; A61B 2017/00314; A61B 2017/00318; A61B 2017/00323; A61B 2017/00327; A61B 2017/00331; A61M 25/0105; A61M 25/0133; A61M 25/0136; A61M 25/0138; A61M 25/0141; A61M 25/0144; A61M 25/0147; A61M 25/0152; A61M 25/0155; A61M 25/0158
USPC .................. 600/107, 139–152; 604/528
See application file for complete search history.

(56) References Cited

U.S. PATENT DOCUMENTS

| | | | |
|---|---|---|---|
| 4,832,473 A | 5/1989 | Ueda | |
| 5,167,221 A | 12/1992 | Chikama | |
| 5,170,775 A * | 12/1992 | Tagami | G02B 23/26 348/75 |
| 5,179,934 A * | 1/1993 | Nagayoshi | A61B 1/00183 600/152 |
| 5,512,035 A | 4/1996 | Konstorum et al. | |
| 5,888,192 A | 3/1999 | Heimberger | |
| 6,117,071 A | 9/2000 | Ito et al. | |
| 8,790,250 B2 | 4/2014 | Petersen | |
| 9,125,582 B2 | 9/2015 | Petersen | |
| 2001/0023313 A1 * | 9/2001 | Ide | A61B 1/00137 600/142 |
| 2005/0131279 A1 * | 6/2005 | Boulais | A61B 1/00059 600/141 |
| 2007/0232858 A1 * | 10/2007 | Macnamara | A61B 1/0052 600/149 |
| 2007/0299311 A1 * | 12/2007 | Sato | A61B 1/00071 600/146 |
| 2008/0051694 A1 * | 2/2008 | Kato | A61B 1/00071 604/22 |
| 2008/0249362 A1 | 10/2008 | Jiang et al. | |
| 2010/0121147 A1 * | 5/2010 | Oskin | A61B 1/0051 600/118 |
| 2011/0306831 A1 | 12/2011 | Køhnke et al. | |
| 2012/0220828 A1 * | 8/2012 | Iwasaki | A61B 1/00188 600/109 |
| 2013/0137924 A1 * | 5/2013 | Iwasaki | A61B 1/00096 600/109 |

FOREIGN PATENT DOCUMENTS

| | | |
|---|---|---|
| EP | 2067433 A1 | 6/2009 |
| JP | 2003-052618 | 2/2003 |
| JP | 2005-237608 | 9/2005 |
| WO | WO2010/066789 | 6/2010 |

OTHER PUBLICATIONS

International Search Report in corresponding International Application No. PCT/DK2013/050049; dated Apr. 24, 2013; 3 pages.
Examination Report issued by the European Patent Office, dated Oct. 24, 2016, in related European Patent Application No. 13708341.6-1666; 4 pages.

* cited by examiner

APPARATUS FOR MAINTAINING A TENSIONED PULL-WIRE IN AN ENDOSCOPE

CROSS REFERENCE TO RELATED APPLICATION

This is a § 371 application of International Application No. PCT/DK2013/050049, entitled "Means for Maintaining a Tensioned Pull-Wire in an Endoscope," filed on Feb. 22, 2013, the full disclosure of which is expressly incorporated herein by reference in its entirety.

TECHNICAL FIELD

The present invention relates to endoscopes in general and more specifically to an apparatus for maintaining a tensioned pull-wire in an endoscope.

BACKGROUND OF THE DISCLOSURE

Endoscopes are well known devices for visually inspecting inaccessible places such as human body cavities. Typically, the endoscope comprises an elongated insertion tube with a handle at the proximal end as seen from the operator, and visual inspections means, such as a built in camera, at the distal end of the elongated insertion tube. This convention of distal and proximal, proximal being the end closest to the operator and distal being the end remote from the operator, as used above for the endoscope in general will, where applicable, be adhered to for all parts throughout this description. Electrical wiring for the camera and other electronics such as LED lighting run along the inside of the elongated insertion tube from the handle to the tip at the distal end. Instead of using cameras, endoscopes may also be fibre-optic, in which case the optical fibres run along inside of the elongated insertion tube. Also, a working channel may run along the inside of the insertion tube from the handle to the tip, e.g. allowing liquid to be removed from the body cavity or allowing the insertion of surgical instruments or the like into the body cavity.

Furthermore, in order to be able to maneuver the endoscope inside the body cavity, the distal end of the endoscope may comprise a section with increased flexibility, e.g. an articulated tip part allowing the operator to bend this section. Typically this is done by tensioning or slacking pull-wires in a guide tube also running along the inside of the elongated insertion tube from the articulated tip part to a control mechanism with a control knob in the handle in an arrangement commonly known as a Bowden cable, cf. Bowden's original patent U.S. Pat. No. 609,570.

The pull-wire running along the inside of the guide tube of a Bowden cable normally extends with a predetermined length over either end allowing an operating member to be attached to a free end, in the following referred to as the proximal end, and an operated member to attached to the other free end, in the following referred to as the distal end. When the ends of the guide member are held stationary, movement of the proximal end of the pull-wire with respect to the guide tube is transmitted to the distal end as a corresponding movement of the distal end of the pull-wire with respect to the guide tube, so as to effect a movement of the operated member.

It is a known problem with Bowden cables is that the functioning of the Bowden cable is influenced by changes in the relative lengths of the pull-wire and guide tube with respect to each other. If the relative lengths change, the ends of the guide tube may be still be considered stationary but the starting point of the transmitted motion is changed. This, in turn, means that the starting point of the motion effecting the movement has and also changed, and the movement is not transmitted as desired to the operated member. In practice, the length of the distal free end of the pull-wire must be maintained with respect to the distal end of the guide tube, which can be considered a stationary reference point for the distal end of the pull-wire. Causes for such changes in the relative lengths of the pull-wire and the guide tube could be the pull-wire stretching, e.g. under tension, or the guide tube shortening, e.g. under compression or due to shrinking of the material of the guide tube due to ageing.

In conventional disposable endoscopes, where manufacturing costs have to be kept down, the guide tube is made of a polymer plastic. Polymer plastics are prone to shrinking, as they deform plastically under tension or pressure over time, in particularly if the temperature increased above room temperature, e.g. during transport or storage in a container in the sun.

If, in an endoscope, the relative length of the pull-wire as compared to the guide tube increases, the movement of the control knob is only transferred in part to the operated member, i.e. the articulated tip part, because the tension of the pull-wire changes, and effectively the starting point of the motion moves accordingly. This leads to a smaller maximum deflection of the articulated tip when the control knob is moved to its most extreme position in the handle, i.e. where further motion is limited by abutting the handle.

This problem of reduced deflection of tips of endoscopes has been dealt with in the prior art, e.g. in U.S. Pat. Nos. 5,167,221, 4,203,430.

U.S. Pat. No. 5,167,221 discloses an endoscope having means for tensioning the pull-wires, e.g. before shipping, during use if the pull-wire slacks over time, or for fine adjustment. This is generally achieved by forming the housing of the handle in two housing parts, which may move with respect to each other in a telescopic manner. The proximal ends of the pull-wires are fixed to the control knob of the control mechanism in one of the housing parts, whereas the proximal ends of the guide tubes abut the other housing part. In one embodiment the two housing parts may be moved with respect to each other using a threaded circumferential ring engaging a corresponding thread on one of the housing parts. This arrangement is quite complicated and does not lend itself to disposable endoscopes, where the manufacturing costs have to be kept down.

U.S. Pat. No. 4,203,430 discloses an arrangement where the proximal ends of the pull-wires are terminated in internally threaded adjustment cylinders which engage an externally threaded part of the racks of a rack and pinion control means. By rotating the cylinders the tension of the control wires may be adjusted. Since, however, the racks, pinion, and adjustment cylinders are all located inside the handle housing such an arrangement is unsuitable for a disposable endoscope because the handle housing would need to be taken apart for adjustment prior to use if the guide tube has shrunk during storage.

SUMMARY OF DISCLOSED EMBODIMENTS

Based on this prior art it is the object of the present invention to provide an endoscope, preferably a disposable endoscope, which is ready for use even if the relative lengths between the inner pull-wire and the outer guide tube has changed because the guide tube has shrunk between the time of manufacture and the time of use.

According to a first aspect of the invention this object is achieved by a control mechanism for an endoscope comprising a Bowden cable with an outer guide tube having a first length between a proximal and a distal end of said outer guide tube and an inner pull-wire having a second length between a proximal end and a distal end of said inner pull-wire, said second length being longer than said first length, characterized in that the outer guide tube comprises a first guide tube section and a second guide tube section, where said first guide tube section has plastic and elastic properties, which are different from the plastic and elastic properties of said second guide tube section.

The use of two sections with different plastic and elastic properties allows the use of a highly flexible material, which is not prone to shrinking under tension during storage and the like over a part, preferably a major part, of the length of the endoscope, i.e. along the inside of the insertion tube. On the other hand the use a different material, which is more rigid but prone to shrinking, reduces the overall shrinking to an acceptable level, where it does not influence the functioning of the endoscope. At the same time the use of such a more rigid material, removes the need for additional support of the Bowden cable, i.e. in addition to a terminating means for the outer guide tube, within the operating handle housing, which would otherwise be necessary in order to avoid meandering or warping of the Bowden cable under the tension applied during use. Such meandering and warping is inter alia undesired because of the increased friction and wear on the pull-wire. The operating handle housing may thus be made less complicated to manufacture, as compared to a solution where the entire outer guide tube is made out of the more flexible material. Thus, because the shrinking of the outer guide tube can only happen over short length thereof the shrinking is negligible and consequently the distal end is for all practical purposes maintained in the desired position where can be considered a stationary reference point for the distal end of the pull-wire. Any shrinking of the outer guide tube will thus not result in any change in the length of the distal free end of the pull-wire. Thus, when the pull-wire is tensioned or slacked during operation, the starting point of the pull-wire with respect to the reference point is as designed and expected and full deflection of the tip, or whatever else the Bowden cable may be intended to control is under full control by the operator.

According to a second aspect of the invention the object is also achieved by an endoscope comprising a control mechanism with a Bowden cable according to the first aspect of the invention, i.e. an endoscope comprising a control mechanism with a Bowden cable having an outer guide tube having a first length between a proximal end and a distal end of said outer guide tube and an inner pull-wire having a second length between a proximal end and a distal end of said inner pull-wire, said second length being longer than said first length characterized in that the outer guide tube comprises a first guide tube section and a second guide tube section, where said first guide tube section has plastic and elastic properties, which are different from the plastic and elastic properties of said second guide tube section.

According to preferred embodiment of the first and second aspects of the invention, said first guide tube section comprises steel. Steel is stable against compression at normal temperatures, i.e. temperatures to which one would expect an endoscope to be exposed, and may, in accordance with a further preferred embodiment, easily be formed into a flexible first guide tube section by forming it into a tightly wound helical coil spring, in which case the first guide tube section may consist solely of steel.

According to a further preferred embodiment of the first and second aspects of the invention, said second guide tube section comprises polymer plastic. Polymer plastics used for the second guide tube section allow this section to be made in a cheap manner, while maintaining good resistance to meandering and warping. This, in turn, allows the operating handle of the endoscope to be made more simple, e.g. without other supports along the length of the second guide tube section than those necessary for maintaining it in a fixed relationship with the operating handle housing and/or the bearings of control knob to which the pull-wires are connected. Furthermore, the use of a polymer plastic tube for the second guide tube section provides an advantage in that unlike the tightly wound coil spring, it may be easily adapted to the correct length during manufacturing using a simple wire stripping tool. That is to say, during manufacture, the guide tube of the pre-fabricated Bowden cable assembly, i.e. first guide tube section, the second guide tube section joined on the pull-wire using a sleeve, may readily be cut to length while in place on the pull-wire. If the guide tube comprised only a tightly wound helical coil spring this would be very difficult, as the precise location of the wound member had to be identified on the circumference and the wound member cut, without damaging the pull-wire. Using a simple wire stripping tool would most likely just result in the tightly wound helical coil spring being stretched rather than cut.

According to another preferred embodiment of the first and second aspects of the invention, said first guide tube section is arranged towards the distal end of said outer guide tube and wherein said second guide tube section is arranged towards the proximal end of said outer guide tube. Having the first guide tube section arranged towards the distal end provides a guide tube with high flexibility so as to the least possible reduce the flexibility of the insertion tube in which it is located and by which it is supported against meandering, while having the second guide tube section arranged towards the proximal end, provides high resistance to meandering within the operating handle housing as explained above.

According to yet a further preferred embodiment of the first and second aspects of the invention, the first tube section abuts the second tube section at an intermediate point between the proximal end and the distal end of said outer guide tube. It has been found that in this way the guide tube may be assembled simply by a short external sleeve accommodating both the first guide tube section and the second guide tube section. This arrangement may be maintained simply by the longitudinal compression forces, with which the outer guide tube is biased anyway. A very simple connection is thus provided.

According to yet another preferred embodiment of the first and second aspects of the invention, said second guide tube section has a length adapted to allow said intermediate point to be located within an operating handle of an endoscope. Thus, full advantages of the flexibility of the first guide tube section within the insertion tube of the endoscope as well as the rigidity of the second guide tube section, as mentioned above, are gained.

According to yet a further preferred embodiment, the control mechanism comprises two Bowden cables, each having a first tube section, a second tube section and an intermediate point, wherein the intermediate points are located at different distances from the proximal end segment of the articulated tip part. Staggering the location of the two intermediate points where the respective guide tube sections abut ensures that sufficient room for making the assembly, even when the internal cross-sectional area of the insertion tube is very small, or when the working channel is large and occupies a large part of the internal cross-section.

According to a third aspect of the invention the object is achieved by a control mechanism for an endoscope comprising an operating handle with an operating handle housing, said control mechanism comprising a Bowden cable with an outer guide tube having a first length between a proximal end and a distal end of said outer guide tube and an inner pull-wire having a second length between a proximal end and a distal end of said inner pull-wire, said second length being longer than said first length, a termination means located within said operating handle housing and adapted to engage the proximal end of the outer guide tube, characterized in that said termination means is movable with respect to said pull-wire and biased towards said engagement with the proximal end of said outer guide tube. Preferably, the bias is applied and upheld automatically, i.e. without intervention of the operator.

This ensures that any shrinking of the outer guide tube is taken up at the proximal end thereof whereas the distal end is maintained in the desired position where can be considered a stationary reference point for the distal end of the pull-wire, any shrinking of the outer guide tube will thus not result in any change in the length of the distal free end of the pull-wire. Thus, when the pull-wire is tensioned or slacked during operation, the starting point of the pull-wire with respect to the reference point is as designed and expected and full deflection of the tip, or whatever else the Bowden cable may be intended to control, is under full control by the operator.

According to a fourth aspect of the invention the object is also achieved by an endoscope comprising a control mechanism with a Bowden cable according to the third aspect of the invention, i.e. an endoscope comprising an operating handle with an operating handle housing, a control mechanism comprising a Bowden cable with an outer guide tube having a first length between a proximal end and a distal end of said outer guide tube and an inner pull-wire having a second length between a proximal end and a distal end of said inner pull-wire, said second length being longer than said first length, a termination means located within said operating handle housing and adapted to engage the proximal end of the outer guide tube, characterized in that said termination means is movable with respect to said pull-wire and biased towards said engagement with the proximal end of said outer guide tube. Also according to this aspect of the invention, the bias is preferably applied and upheld automatically, i.e. without intervention of the operator.

According to a preferred embodiment of the third and fourth aspects of the invention, said termination means comprises a linearly displaceable part movable with respect to said housing. Using a linearly displaceable part allows the same termination means to be used with both sides of a dual Bowden cable arrangement, as preferably used for maneuvering the articulated tip part of the endoscope, because the two outer guide tubes of the respective Bowden cable arrangements are of the same length and thus equally prone to shrinking.

According to a further preferred embodiment of the third and fourth aspects of the invention, said displaceable part is spring biased towards the distal end of said outer guide tube. Spring bias of a linear motion is readily achievable using a coil spring attached to a suitable fixed point in the operating handle housing.

According to a specifically preferred embodiment according of the third and fourth aspects of the invention, said displaceable part comprises a first part uni-directionally moveable within a second part. By the use of this arrangement the movable part of the termination means need not be directly movable with respect to parts of the operating handle housing, and the operating handle housing need not itself have design features specifically directed to allow the linear motion of the termination means.

Consequently, according to a further preferred embodiment of the third and fourth aspects of the invention, said second part is adapted to he accommodated in a seat provided on an internal housing wall of said operating handle housing. This allows the operating handle housing to be of the very same construction irrespective of whether the present invention is implemented according to the first, second, third or fourth aspect of the invention.

BRIEF DESCRIPTION OF THE DRAWINGS

The invention will now be described in greater detail based on non-limiting exemplary embodiments and with reference to the drawings, on which.

DETAILED DESCRIPTION

Figures 1, 2:
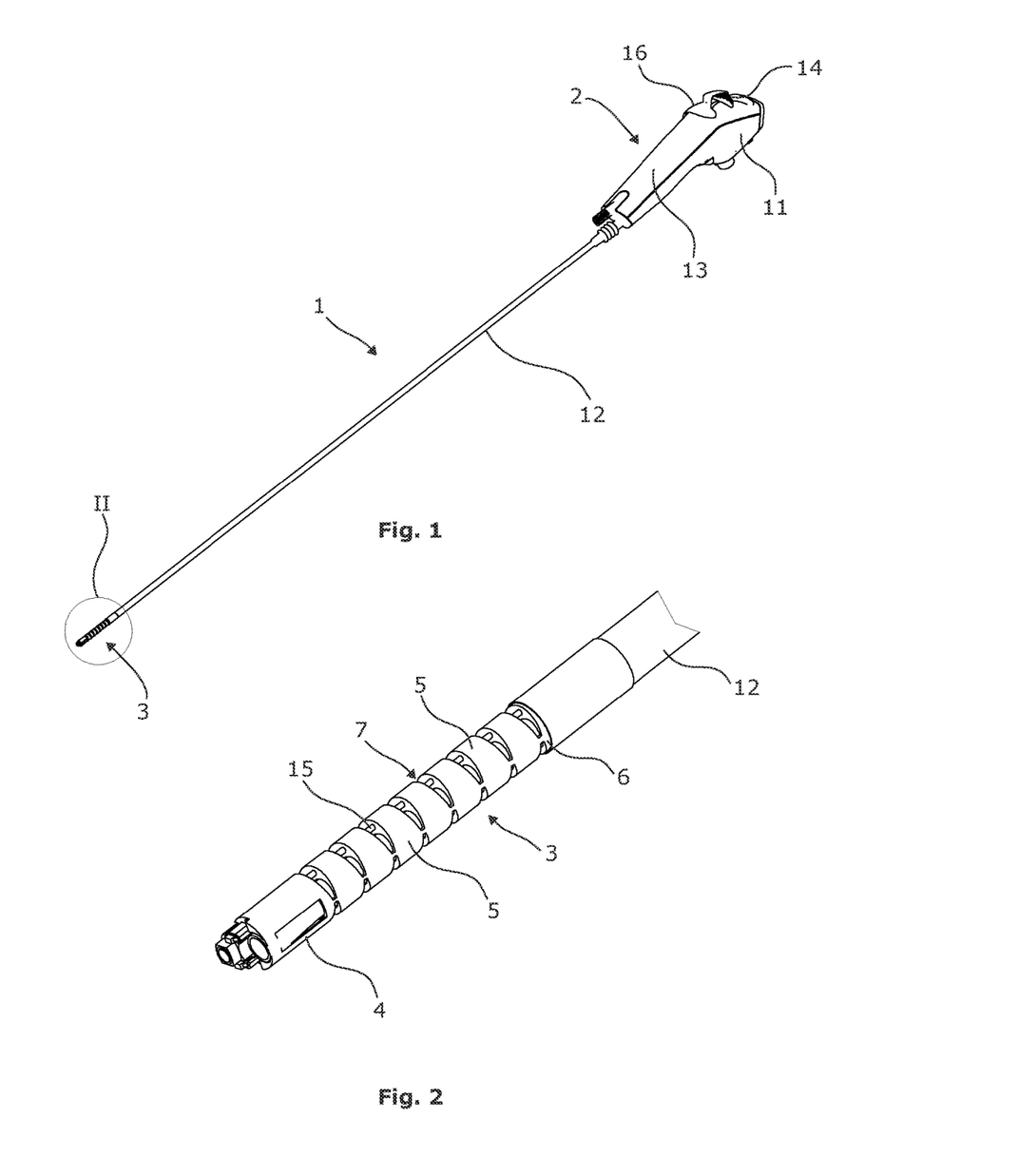
FIG. 1 shows a perspective view of an endoscope with some parts removed for clarity in the detail II.
FIG. 2 shows a details of an articulated tip part of an endoscope with outer sheathing removed for clarity.

In FIG. 1 an endoscope 1 is shown in overall perspective view. The endoscope 1 comprises an operating handle 2 at the proximal end, i.e. the end closest to an operator. The operating handle 2 comprises an upper housing part 13 and a lower housing part 11. A somewhat flexible insertion tube 12 extends from the operating handle 2. At the distal end of the insertion tube 12 an articulated tip part 3 is provided. The articulated tip part 3 inter alia allows the insertion tube 12 to be guided through a somewhat tortuous path of a body cavity. For illustration purposes the outer sheath of the insertion tube 12 has been removed at the articulated tip part 3 in the circle II in FIG. 1. The circle II corresponds to FIG. 2, in which the articulated tip part 3 is shown in greater detail.

For maneuvering the articulated tip part 3 a control knob 14 forming part of the control mechanism of the endoscope 1 protrudes from the operating handle 2 through the upper housing part 13 thereof. During storage of the endoscope 1, the control knob 14 may be covered by a removable securing clip 16, which is to be removed prior to use.

Figure 3:
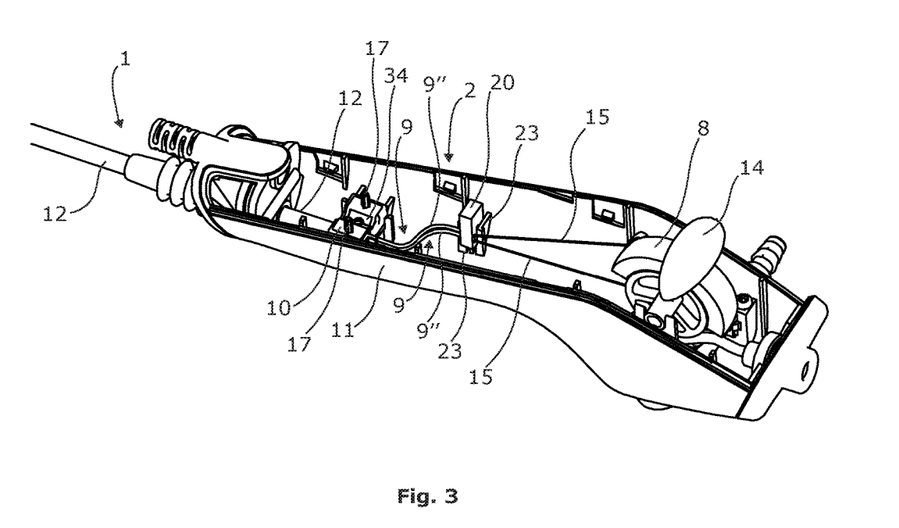
FIG. 3 is a perspective view of the shows the interior of the lower housing part of the operating handle housing of the endoscope according to the first and second aspects of the invention.
Figure 5:
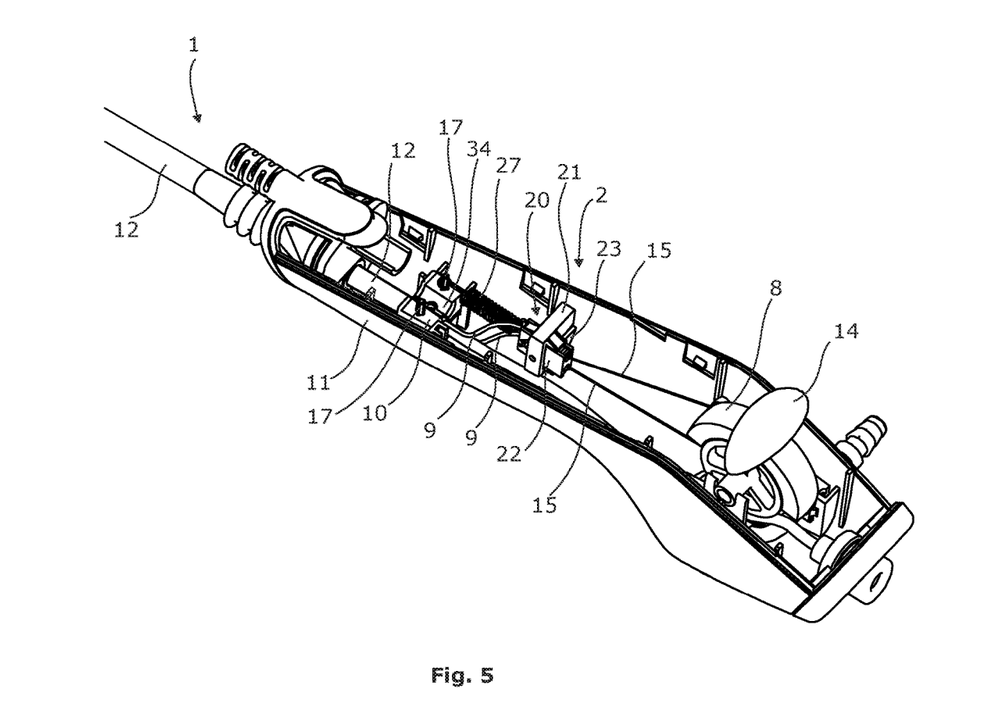
FIG. 5 is a perspective view of the shows the interior of the lower housing part of the operating handle housing of the endoscope according to the third and fourth aspects of the invention.

The articulated tip part 3 comprises a number of hinged segments 4, 5 separated by V-shaped cut-outs 7. More specifically the articulated tip part 3 comprises a distal end segment 4, a proximal end segment 6 (only partially visible) and a number of intermediate segments 5. A pair of symmetrically arranged pull-wires 15, of which only one is visible in FIG. 2, are connected to the distal end segment 4 and guided through suitable passages in the intermediate segments 5 and the proximal end segment 6. These pull-wires 15 form part of a pair of Bowden cables leading to the operating handle 2, in which the proximal ends of the pull-wires are connected to a lever 8 connected to the control knob 14, as can be seen in FIGS. 3 or 5.

By tensioning the pull-wire 15 on one side and slacking it on the other side, the articulated tip part 3 may be deflected to one side collapsing the V-shaped grooves 7 on that side and expanding them on the opposite side. In order to achieve full deflection, it is important that the pull-wire 15 may be pulled sufficiently far back into the insertion tube 12 before the control knob 14 or the lever 8 thereof abuts the operating handle housing 13 of the operating handle 2.

Between the articulated tip part 3 and the operating handle 2 each of the pull-wires 15 are located as the inner pull-wires 15 inside an outer guide tube 9. The distal end of the outer guide tube 9 is in a fixed positional relationship with the proximal end segment 6 of the articulated tip part 4, in a manner known per se for Bowden cables, e.g. by being biased into abutment in suitable bores therein, or by being glued or otherwise connected to the proximal end segment 6. The proximal end of the guide tubes 9 extend out of the insertion tube 12 inside the operating handle 2, as can be seen in FIGS. 3 or 5, in both of which the upper housing part 13 has been removed for illustration purposes.

The outer guide tube 9 has a first length between the proximal end inside the operating handle 2 and the distal end of the outer guide tube 9 at the proximal end segment 6 of the articulated tip part 3. The inner pull-wire 15 has a second length between the proximal end at the lever 8 connected to the control knob 14 and the distal end of said inner pull-wire 15 connected to the distal end segment 4 of the articulated tip part 3. The second length is longer than said first length so as to leave free ends of the pull-wire 15 extending at both the distal end of the guide tube 9 and the proximal end of the guide tube.

Referring now to FIG. 3, it can be seen that the proximal end of the insertion tube 12 is fixed in the operating handle 2 by a clamp 10 securing it to the inside of the lower housing 11. The clamp 10 may be fastened using screws but preferably, it is simply clicked onto two protrusions 17 provided on the inner housing wall or on a lower clamping part (not visible). As can be seen the clamp 10 has a semi-circular cut-out 34 in the upward facing, surface. A further semi-circular cut-out (not visible) is provided in the invisible downward facing surface of the clamp 10. The diameter of the (invisible) downward facing cut-out in the clamp 10 corresponds to the external diameter of the insertion tube for good clamping, whereas the upward facing cut-out 34 has a different diameter, allowing the same clamp 10 and handle 2 to be used in an endoscope with an insertion tube 12 with a different diameter, simply by turning the clamp 10 upside down before mounting it. The number of necessary parts to be manufactured and stored may thus be reduced. The skilled person will realize clamping is only a preferred way of securing the insertion tube 12 to the operating handle 2 and that the insertion tube 12 may be secured to the operating handle in numerous other ways. The proximal ends of the outer guide tubes 9 of the Bowden cables extend from the proximal open end of the insertion tube 12 and into engagement with a terminal block 20, preferably by abutting into suitable bores thereof as known per se for Bowden cables. The bores are not visible in FIG. 3, but correspond essentially to reference numeral 32 of the termination means of the embodiment of FIG. 5, to be explained below. The pull-wires 15 are suitably pre-tensioned to transmit a biasing force all the way from the distal end segment 4 of the articulated tip part 3, via the intermediate segments 5 and the proximal end segment 6 to the distal end of the outer guide tube 9 and all the way back to the proximal end of the guide tube 9 into abutment thereof with the terminal block 20. Within the insertion tube 12 the outer guide tube 9 may to some extent receive support against meandering or warping by internal walls of the insertion tube 12. Between the proximal end of the insertion tube 12 and the terminal block 20 the guide tube 9 is not supported as such, but, as can be seen, follows an unsupported S-curve inside the operating handle 2. If the outer guide tube 9 shrinks, the distal end of the outer guide tube 9 would move closer to the terminal block, leaving a longer, or at least less tensioned, free distal end of the pull-wire 15 in the articulated tip part 3, i.e. between the fixed reference point constituted by the proximal end segment 6, to the distal end segment 4 of the articulated tip part 3. In that case it is not ensured that the V-shaped grooves 7 are fully collapsed, and consequently not ensured that the articulated tip part 3 deflects in full.

Figure 4:
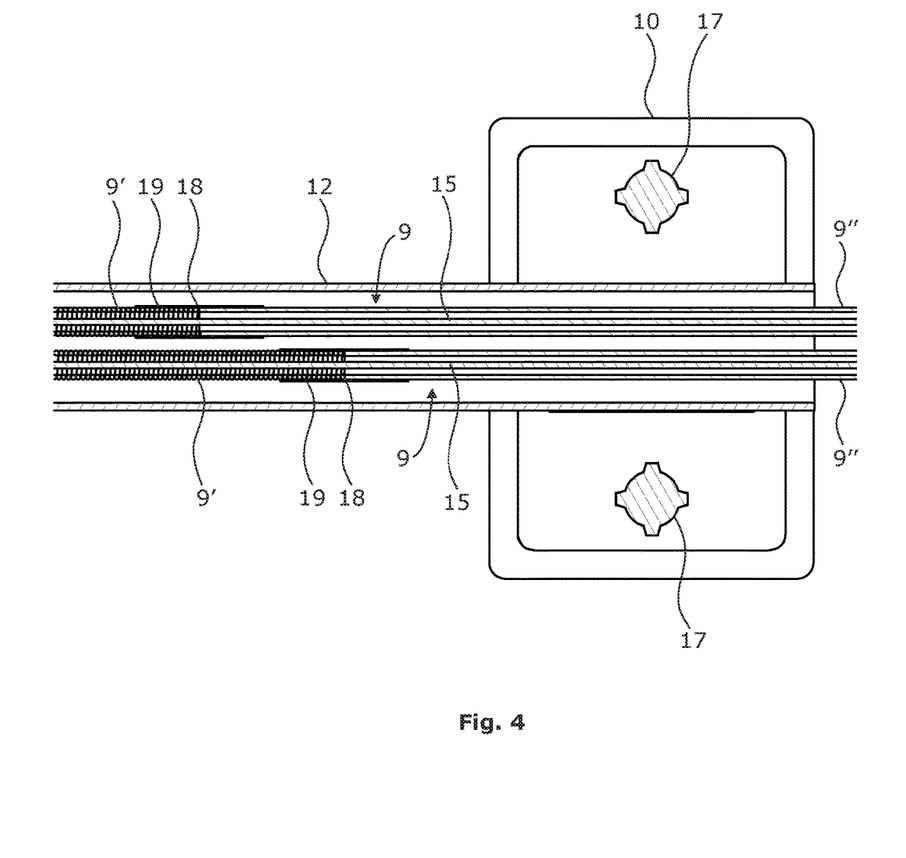
FIG. 4 shows a partial cross section of a detail of an embodiment of the Bowden cables according to the first and second aspect of the invention.

To overcome this, the outer guide tube 9 has, as can be seen in FIG. 4 been constructed from two outer guide tube sections 9' and 9". The outer guide tube 9 thus comprises a first guide tube section 9' and a second guide tube section 9". According to the first and second aspects of the invention, the first guide tube section 9' has plastic and elastic properties, which are different from the plastic and elastic properties of said second guide tube section 9". More specifically the first guide tube section 9' comprises steel, which under the temperature conditions that a disposable endoscope is exposed to hardly deforms plastically. Preferably, the steel comprised in the first guide tube section 9' comprises a tightly wound helical coil spring, i.e. with no gaps between adjacent windings in the relaxed condition where no substantial external forces act upon it. Such a helical coil spring is as such well known in Bowden cables, e.g. from U.S. Pat. No. 6,117,071 where a single Bowden cable is used to focus the optics in the distal end of the endoscope, or even from Bowden's original patent U.S. Pat. No. 609,570. This imparts the first guide tube section 9' a high degree of bending elasticity and flexibility, at least as compared to the situation where the second guide tube section 9" comprises a polymer plastic material, such as Isoplast 2510 polyurethane, in particular in the shape of a tube. The polymer plastic of the tube may, on the other hand, behave plastically under the temperature conditions that a disposable endoscope is exposed to, in particular when compressed between the proximal end segment 6 of the articulated tip part 3 and the terminal block 20 by the pull-wire 15.

The use of a polymer plastic tube provides a further advantage, because as compared to the tightly wound coil spring, it may be easily adapted to the correct length during manufacturing using a simple wire stripping tool. That is to say, during manufacture, the guide tube 9 of the pre-fabricated Bowden cable assembly, i.e. first guide tube section 9', the second guide tube section 9" joined on the pull-wire 15 using a sleeve 19, may readily be cut to length while in place on the pull-wire 15. If the guide tube 9 comprised only a tightly wound helical coil spring this would be very difficult, as the precise location of the wound member had to be identified on the circumference and the wound member cut, without damaging the pull-wire 15. Using a simple wire stripping tool would most likely just result in the tightly wound helical coil spring being stretched rather than cut.

In accordance with the first and second aspect of the invention the length of the first guide tube section 9' is substantially longer than the length of the second guide tube section 9", e.g. 10 or 20 times longer or more. Thus, even if the second guide tube section 9" shrinks, the effect becomes negligible as because the vast major of the overall length of the outer guide tube 9 does not shrink. The length of the second tube section 9" may be made very short, i.e. a few centimeters. This is because only those few centimeters, e.g. 3 to 4 centimeters, located inside the operating handle 2 without any additional support than the terminal block 20, need to have the rigidity to withstand the tendency to meander or warp, under the forces of the pull-wire 15.

Since the outer guide tube 9 is compressed between the proximal end segment 6 of the articulated tip part 3 and the terminal block 20 by the pull-wire 15 it has been realised that making the outer guide tube 9 from two guide tube sections 9', 9" can be very simple. Preferably, the guide tube 9 is made simply by joining the two guide tube sections 9' and 9" in an abutting engagement inside a bushing 19 at an intermediate point 18. Preferably, this intermediate point 18 is located inside that part of the insertion tube 12, which is located inside the operating handle 2, in this part of the insertion tube 12, the lack of flexibility of the second guide tube section 9" is of little importance as the insertion tube 12 itself does not need to flex. Furthermore the wall of the insertion tube 12 will support the bushing 19 in the lateral direction, thus keeping the abutting ends of the two guide tube sections 9', 9" in their abutting engagement. Depending on the dimensions of other parts of the endoscope 1, bushing 19 may advantageously be constructed from a short length of tubing used for other purposes in the endoscope 1, e.g. the tube for a working channel, made from the polyurethane Pellethane 2363 80AE.

As can be seen from FIG. 4, in the endoscope, which, in the embodiment described, has two pull-wires 15, the two bushings 19 and consequently the two intermediate points are staggered a little with respect to each other. That is to say, even though located within the part of the insertion tube 12, preferably within the part of the insertion tube 12 Which is located inside the operating handle 2, the intermediate points 18 are located at different distances from the proximal end segment 6 of the articulated tip part 3. The bushings 19 will thus not conflict with each other in the limited space inside the insertion tube 12.

Turning now to FIG. 5 an embodiment according to the third and fourth aspects of the invention, is shown. As will be seen the endoscope 1 depicted in FIG. 5 is largely identical to that of FIGS. 1-3, differing essentially in the use of a different outer guide tube 9, and the construction of the termination of the outer guide tube 9 within the operating handle 2 necessitated by the use of the different guide tube 9.

More specifically, the guide tube 9 of FIG. 5 is constructed in a conventional manner as a single tube of polymer plastic material extending all the way from the proximal end segment 6 of the articulated tip part 3 to the terminal block 20. It is thus prone to shrinking, which for the reasons explained above is undesired. To compensate for this shrinking, i.e. in order to secure the engagement of the distal end of the outer guide tube 9 in firm engagement with proximal end segment 6 of the articulated tip part 3, so as to have a well defined reference point for the pull-wire 15, a different termination means is used.

Figure 6:
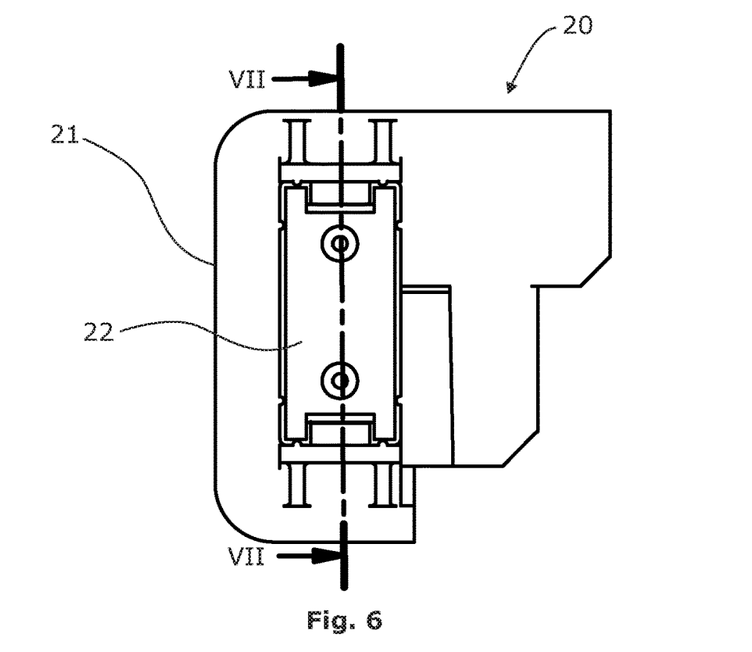
FIG. 6 shows a terminating means according to the third or fourth aspect of the invention.
Figure 7:
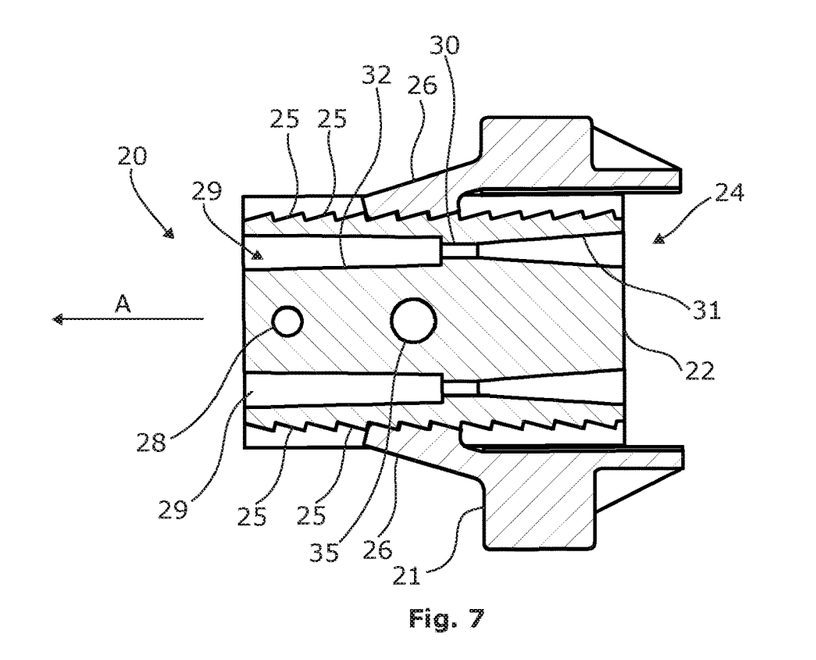
FIG. 7 shows a cross section of the terminating leans of FIG. 6 along the lines VII-VII in FIG. 6.

As can be seen from FIGS. 6 and 7 the termination means provided as the terminal block 20 is constructed from two parts, a first outer block part 21 and a second inner block part 22. The first outer block part 21 has dimensions allowing it to be held in fixed engagement with suitable seating means 23 arranged on the inner wall of the lower operating handle housing part 11. Preferably, these dimensions correspond to the dimensions of the terminal block 20 used as the termination means in the embodiment according to FIGS. 1-3. This allows the use of the same lower housing part 11 of the operating handle 2 for this embodiment too, thus reducing the number of different parts to be manufactured and stored.

As best seen in the cross-section of FIG. 7, the first outer block part 21 has a central through hole 24, through which the inner second block part 22 may slide. The inner block part 24 comprises a number of suitable teeth 25 engaging a likewise toothed resilient tab 26 formed on the outer block part 21, so as to form a ratchet and rack mechanism, allowing only uni-directional motion of the inner block part 22 with respect to the outer block part 21, viz. in the direction of the arrow A. Preferably the inner block part 22 is symmetrical, having a ratchet and rack mechanism on either side.

The inner block part 22 has two passages 29 for the passing the pull-wire 15 through. The passages 29 have varying diameters. The middle part 30 of the passage corresponds largely to the diameter of the pull-wire 15. From the middle part 30 towards the proximal end of the passage 29 it comprises a proximal part 31 where it is flared out in order to allow free passage of the pull-wire 15 at an angle to the lever 8 of the control knob 14. At the distal end of the passage 29, the passage 29 comprises a distal part 32 where diameter is increased to accommodate the proximal end of the outer guide tube 9. The distal part 33 of the passage 29 is generally cylindrical or only slightly frusto-conical.

When the outer block part 21 is appropriately located in the seating means 23 on the inside of the lower operating handle housing part 11, the inner block will only be able to slide linearly in the direction towards the distal end of the endoscope 1 or in effect the distal end of the outer guide tube 9. In order to effect this motion the inner block part 22 is spring biased, preferably by means of a coil spring 27. The coil spring 27 is at one end to the inner block part 22, preferably anchored in an anchoring hole 28 in the inner block part 22. The other end of the coil spring 27 is anchored to a suitable fixed part within the operating handle 2, such as the lower operating handle housing 11 or, as preferred, the clamp 10 securing the insertion tube 12. As can be seen this could be achieved by simply anchoring the coil spring 27 to the protrusions 17.

The coil spring 27 is preferably a tension spring pulling at the inner block part 22 with suitable force to maintain the inner block part 22 in firm engagement with the proximal end of the outer guide tube 9, but without deforming the Bowden cable and pulling the inner block part 22 out of the outer block part 21. However, if the this balance of forces is changed, that is if the outer guide tube 9 shrinks, the opposing force on the coil spring 27 is reduced and the coil spring 27 is able to move the inner block part 22 in the outer block part 21 to maintain—or rather regain the opposing force. Regaining rather than maintaining is to be understood as slight variations in force, because additional force is necessary to allow the ratchet and rack to move one tooth with respect to each other. The biasing force is thus applied and upheld automatically, i.e. without intervention of the operator. Since the force on the proximal end of the outer guide tube 9 is generally maintained this way, the force keeping the distal end of the outer guide tube 9 in firm engagement with the proximal end segment 6 of the articulated tip part 3 is also automatically maintained. Consequently, the reference point for the distal free end of the pull-wire 15 is maintained, and full deflection of the articulated tip part 3 during operation is ensured. This happens automatically without the need for any intervention of the user prior to use of the endoscope 1. In order to avoid inadvertent displacement of the inner block part 22 with respect to the outer block part 21 during mounting, e.g. when attaching the coil spring 27 to the inner block part 21 in the anchoring hole 28 thereof or to the protrusions 17 the two parts may temporarily be secured to each other. For this inner block part 22 comprises a through hole 35, which may be aligned with a corresponding hole in the outer block part, an secured temporarily with a pin or other suitable tool.

The above description has provided two solutions to the shrinking problem of the outer guide tube 9 in an endoscope 1, both of which may be implemented in otherwise identical endoscopes 1. In fact, both solutions may also be implemented in one and the same endoscope 1, i.e. an endoscope with a two part guide tube 9 according the first and second aspects of the invention is terminated using a two part terminal block 20 according to the third and fourth aspect of the invention.

The embodiments described in above description of how to implement the solutions of the invention are only examples. The skilled person will realize that numerous variations to the solutions may be presented without departing from the scope of the invention. In particular, the solutions may he implemented in endoscopes differing in construction from those used in the exemplary embodiments. Also, the skilled person will realize that e.g. material choices and dimensions may vary. The skilled person will also understand that the above description of the exemplary embodiments refer to those embodiments in a neutral relaxed state, i.e. when the endoscopes are not in use, and not influenced by external forces.

The invention claimed is:

1. An endoscope comprising:
an operating handle housing;
an articulated tip part;
an insertion tube between the operating handle housing and the articulated tip part; and
a control mechanism extending from the operating handle housing to the articulated tip part, the control mechanism including an outer guide tube having a first length between a proximal end and a distal end of said outer guide tube and an inner pull-wire having a second length between a proximal end and a distal end of said inner pull-wire, said second length being longer than said first length, a force applied to the proximal end of the inner pull-wire moving the inner pull wire within the outer guide tube which transmits the force to the articulated tip part to articulate the articulated tip part,
wherein the outer guide tube comprises a first guide tube section comprised of a coiled metal and a second guide tube section comprised of a polymer plastic, wherein the second guide tube section is contained within the operating handle housing and is collinear with the first guide tube section, the first guide tube section arranged toward the distal end of the outer guide tube and the second guide tube section extending from the first guide tube section toward the proximal end of the outer guide tube,
wherein a proximal end of the insertion tube is positioned in the operating handle housing, and
wherein the first guide tube section and the second guide tube section are joined by a bushing and have proximal and distal ends, the bushing, the proximal end of the first guide tube section and the distal end of the second guide section located within the proximal end of the insertion tube in the operating handle housing.

2. An endoscope according to claim 1, further comprising a first termination part supported by the operating handle housing and displaceable, relative to the operating handle housing, toward the outer guide tube to compensate for shrinking of the outer guide tube.

* * * * *